(12) United States Patent
Perrey et al.

(10) Patent No.: US 7,905,835 B2
(45) Date of Patent: Mar. 15, 2011

(54) METHOD FOR ASSESSING MECHANICAL PROPERTIES OF AN ELASTIC MATERIAL

(75) Inventors: Christian Perrey, Mondsee (AT);
Armin Schoisswohl, Wels (AT);
Manfred Aichhorn, Upper Austria (AT);
Helmut Brandl, Pfaffing (AT)

(73) Assignee: General Electric Company, Schenectady, NY (US)

( * ) Notice: Subject to any disclaimer, the term of this patent is extended or adjusted under 35 U.S.C. 154(b) by 538 days.

(21) Appl. No.: 12/014,599

(22) Filed: Jan. 15, 2008

(65) Prior Publication Data
US 2009/0182234 A1 Jul. 16, 2009

(51) Int. Cl.
*A61B 8/00* (2006.01)
(52) U.S. Cl. .................................... 600/438
(58) Field of Classification Search .............. 600/437, 600/438, 443, 447, 449, 587; 73/573, 787–790
See application file for complete search history.

(56) References Cited

U.S. PATENT DOCUMENTS

| | | | | |
|---|---|---|---|---|
| 4,271,706 A * | 6/1981 | Ledley | | 73/614 |
| 5,099,848 A | 3/1992 | Parker et al. | | |
| 5,524,636 A * | 6/1996 | Sarvazyan et al. | | 600/587 |
| 5,546,807 A * | 8/1996 | Oxaal et al. | | 73/606 |
| 6,270,459 B1 * | 8/2001 | Konofagou et al. | | 600/449 |
| 6,482,159 B1 * | 11/2002 | Wiesauer et al. | | 600/443 |
| 6,508,768 B1 * | 1/2003 | Hall et al. | | 600/443 |
| 6,764,448 B2 * | 7/2004 | Trahey et al. | | 600/437 |
| 7,077,807 B2 * | 7/2006 | Torp et al. | | 600/438 |
| 7,223,241 B2 * | 5/2007 | Radulescu | | 600/443 |
| 7,601,122 B2 * | 10/2009 | Zagzebski et al. | | 600/449 |
| 7,632,230 B2 * | 12/2009 | Varghese et al. | | 600/437 |
| 7,678,051 B2 * | 3/2010 | Fan et al. | | 600/438 |
| 2004/0254460 A1 * | 12/2004 | Burcher et al. | | 600/437 |
| 2006/0052696 A1 * | 3/2006 | Shiina et al. | | 600/437 |
| 2007/0093716 A1 | 4/2007 | Radulescu | | |
| 2007/0167772 A1 | 7/2007 | Radulescu | | |

(Continued)

FOREIGN PATENT DOCUMENTS
WO WO 2007/110669 A1 10/2007

OTHER PUBLICATIONS

Brian S. Garra et al., Elastography of Breast Lesions: Initial Clinical Results, 1997, Radiology, vol. 202, pp. 69-86.

(Continued)

*Primary Examiner* — Francis Jaworski
(74) *Attorney, Agent, or Firm* — Dean Small; The Small Patent Law Group (57) ABSTRACT

A method for assessing mechanical properties of an elastic material includes obtaining volumetric ultrasound data sets of the elastic material in two different states of compression. First ultrasound image data of a first hypersurface region of interest (ROI) is selected from a first of the data sets, and second ultrasound image data of a second hypersurface ROI is selected from a second of the data sets. The first ultrasound image data and the second ultrasound image data are compared to determine motion within the elastic material. If out of ROI motion of the elastic material is not less than a specified or predetermined amount and if an allowed number of iterations has not been met, the orientation of at least one ROI is changed and a portion of the process is iterated. Otherwise, an indication of motion resulting from the applied compression within the elastic material is displayed.

20 Claims, 5 Drawing Sheets

U.S. PATENT DOCUMENTS

2007/0238966 A1* 10/2007 Sun et al. .................. 600/407
2010/0094131 A1* 4/2010 Bae et al. .................. 600/438
2010/0312092 A1* 12/2010 Maurice et al. ............ 600/411

OTHER PUBLICATIONS

E.J. Chen et al., Ultrasound Tissue Displacement Imaging with Application to Breast Cancer, 1995, Ultrasound in Med. & Biol., vol. 21, No. 9, pp. 1153-1156, Michigan, USA.

Hiltawsky, K.M. et al., Freehand ultrasound elastography of breast lesions: clinical results, Ultrasound Med. Biol., vol. 27, No. 11, pp. 1461-1469, 2001.

Richard G.P. Lopata et al., 3D Strain Estimation for Isotropic and Anisotropic Materials, Ultrasonics Symposium, 2005 IEEE vol. 2, Issue: Sep. 18-21, 2005, pp. 731-734.

Ako Itoh et al., Breast Disease: Clinical Application of US Elastography for Diagnosis, Radiology, vol. 239, No. 2, pp. 341-350.

* cited by examiner

METHOD FOR ASSESSING MECHANICAL PROPERTIES OF AN ELASTIC MATERIAL

BACKGROUND OF THE INVENTION

This invention relates generally to ultrasound imaging, and more particularly to visualization of tissue elasticity.

Ultrasound can be used to assess mechanical properties of tissue. In particular, ultrasound can be used for visualization of tissue elasticity, which permits the characterization of tissue.

For visualization of tissue elasticity, a tissue is mechanically deformed and scanned with ultrasound during (or both before and after) deformation. The deformation causes displacement and changes in tissue strain, which are estimated from the acquired ultrasound data and visualized. The visualization process is known in the art as "strain imaging." An important application of strain imaging is the detection of lesions in tissue, such as tumors.

This imaging technique is established technique that is used primarily on 2D ultrasound data sets of tissues. A 2D data set is acquired, and the tissue is then compressed followed by the acquisition of a second data set. The technique then includes estimating the tissue motion in one or two dimensions from these data sets. The method has been extended to volume ultrasound by imaging a whole volume and determining 3D tissue motion in all three directions. This 3D tissue motion determination is computationally quite intense and takes some time.

A standard technique for breast ultrasound imaging includes obtaining ultrasound image data of a 3D volume displaying a C plane that is perpendicular to the ultrasound transducer used for imaging. A volume is acquired and a slice is taken as the image that is displayed.

In one known method of 2D strain imaging, axial and lateral strains are estimated from 2D ultrasound B mode scans in which the direction of compression is parallel to the axial ultrasound beam direction. Another known technique is to estimate 3D displacement and strain distributions from ultrasound volume data sets. This method also provides estimates of lateral and elevational strain.

However, the estimation of 3D strain distributions is very computationally intensive and thus not practical for real-time imaging. Also, out of plane motion renders conventional 2D strain imaging less accurate than may be desired. A method and apparatus for real-time estimation of strain imaging that is less subject to problems caused by out of plane motion would thus be desirable.

BRIEF DESCRIPTION OF THE INVENTION

In accordance with an embodiment, a method for assessing mechanical properties of an elastic material using an ultrasound imaging device is provided. The ultrasound imaging device has an ultrasound transmitter, an ultrasound receiver configured to receive reflected ultrasound waves reflected from a region of interest of the elastic material and to convert the received ultrasound waves into image data, a processor configured to analyze the image data, and a display configured to show results from the analysis of the image data. The method includes obtaining a first volumetric ultrasound data set of the elastic material while the elastic material is in a first state of compression, and obtaining a second volumetric ultrasound data set of the elastic material while the elastic material is in a second state of compression. The method further includes selecting first ultrasound image data of a first hypersurface region of interest (ROI) from the first ultrasound volume data set, selecting second ultrasound image data of a second hypersurface ROI from the second ultrasound volume data set, and comparing the first ultrasound image data and the second ultrasound image data to determine motion within the elastic material. Next, a determination is made as to whether out of ROI motion of the elastic material is less than a predetermined amount. If not, and if an allowed number of iterations has not been met, then the method continues by changing an orientation of at least one of the ROIs and iterating the corresponding selection or selections of ultrasound image data, as well as iterating the analyzing and comparing of the first ultrasound image data and the second ultrasound image data and the test of out of ROI motion. Otherwise, the method continues by displaying an indication of motion resulting from the applied compression within the elastic material.

In yet another embodiment, there is provided an ultrasound imaging apparatus. The apparatus includes an ultrasound transmitter, an ultrasound receiver configured to receive reflected ultrasound waves reflected from a region of interest in an elastic material and to convert the received ultrasound waves into image data, a processor configured to analyze the image data, and a display configured to show results from the analysis of the image data. The apparatus is configured to obtain a first volumetric ultrasound data set of the elastic material while the elastic material is in a first state of compression, and obtain a second volumetric ultrasound data set of the elastic material while the elastic material is in a second state of compression. The apparatus is further configured to select first ultrasound image data of a first hypersurface region of interest (ROI) from the first ultrasound volume data set, select second ultrasound image data of a second hypersurface ROI from the second ultrasound volume data set, and compare the first ultrasound image data and the second ultrasound image data to determine motion within the elastic material. The apparatus is further configured to determine whether out of ROI motion of the elastic material is less than a specified or predetermined amount. If not, and if an allowed number of iterations has not been met, then the apparatus is configured to change an orientation of at least one of the ROIs and iterate the corresponding selection or selections of ultrasound image data, as well as iterate the analyzing and comparing of the first ultrasound image data and the second ultrasound image data and the test of out of ROI motion. Otherwise, the apparatus is configured to display an indication of motion resulting from compression within the elastic material.

In yet another embodiment, there is provided a machine-readable medium or media having thereon instructions configured to instruct an ultrasound imaging device having an ultrasound transmitter, an ultrasound receiver configured to receive reflected ultrasound waves reflected from a region of interest in an elastic material and to convert the received ultrasound waves into image data, a processor configured to analyze the image data, and a display configured to show results from said analysis of the image data. The instructions are configured to instruct the apparatus to obtain a first volumetric ultrasound data set of the elastic material while the elastic material is in a first state of compression, obtain a second volumetric ultrasound data set of the elastic material while the elastic material is in a second state of compression, select first ultrasound image data of a first hypersurface region of interest (ROI) from the first ultrasound volume data set, and select second ultrasound image data of a second hypersurface ROI from the second ultrasound volume data set. The instructions are further configured to instruct the apparatus to analyze and compare the first ultrasound image data and the second ultrasound image data to determine motion within the elastic material, and test whether out of ROI motion of the elastic material is less than a specified or predetermined amount. If not, and if an allowed number of iterations has not been met, then the instructions are configured to instruct the apparatus to change an orientation of at least one of the ROIs and iterate the corresponding selection of ultrasound image data, as well as iterate the analyzing and comparing the first ultrasound image data and the second ultrasound image data and the test of out of ROI motion. Otherwise, the instructions instruct the apparatus to display an indication of motion resulting from compression within the elastic material.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

DETAILED DESCRIPTION OF THE INVENTION

As used herein, an element or step recited in the singular and preceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the term "hypersurface" is a surface of arbitrary shape and/or curvature. Although a hypersurface is not necessarily planar, one common example of a hypersurface is a planar surface.

Some embodiments of the present invention provide a method for estimating displacement and strain from volume data sets, where only a hypersurface region of interest (e.g. a plane) is selected. This procedure is particularly useful, for example, for breast exams, where ultrasound volume datasets are acquired and lesions are visualized in the C-plane. Therefore, in some embodiments, tissue hardness is imaged by taking a first image, compressing the tissue being imaged to thereby cause tissue motion, and taking at least a second image. By analyzing and comparing the first image and the second image, the tissue motion is determined.

The amount of motion is related to the hardness of the tissue being compressed. Thus, a very stiff portion of tissue will not result in much tissue displacement, whereas very soft tissue will be significantly displaced. So, by determining the amount of displacement, or more specifically, the derivative of the displacement, regions of the tissue that have high strain and regions that have low strain can be differentiated. The low strain regions relate to harder tissue than the high strain regions. Thus, a technical effect of some embodiments of the present invention is the display of an indication of motion of compressed tissue, and/or a display of high strain and low strain portions of compressed tissue. From this display, an indication of lesions or cancer may be determined, or an indication of the quality of a compressible material may be determined.

Although most of the embodiments described herein are described in connection with the detection of cancerous tissue or lesions, many embodiments of the present invention can be used for other types of discrimination between other types of tissue or even other types of materials. For example, the various embodiments of the invention do not require that the tissue being examined be human or even living tissue, nor is the invention limited to breast examination. For example, the material examined could be any organ from any animal, not just humans. Some embodiments of the invention can be used to sense meat quality. Furthermore, the material can be any compressible material that can be imaged using ultrasound or other incident waves, and thus, some embodiments of the present invention can be used for industrial inspection.

In some embodiments of the present invention, the region of interest (ROI) selected for estimation has an arbitrary orientation within the tissue volume, and an approximate location and orientation of the ROI may be set by the user. However, tissue motion is complex under compression and the displacement estimation may suffer as a result of out of ROI motion. To "fine tune" the ROI location and to enhance estimation results, the initial ROI location is adaptively changed based on selected or preselected optimization criteria, wherein a goal is to select an ROI with an orientation that reduces, and preferably minimizes, out of ROI motion. Some examples of suitable optimization techniques are disclosed in U.S. Patent Application Publication No. US 2007/0093716 to Radulescu, published Apr. 26, 2007, and entitled "Method and apparatus for elasticity imaging."

Predefined orientation settings can be used for selecting the ROI location. In some embodiments, optimizing criteria are used for the validity of the estimation. These validity criteria may comprise, for example, a correlation measure of the two data sets for the first ROI and the second ROI, and/or limits on displacement or strain magnitude.

Embodiments of the present invention thus yield enhanced estimation results compared to conventional 2D strain imaging because out of ROI motion is minimized or at least reduced. Also, the computational load is significantly reduced compared to full 3D strain estimation.

Figure 1:
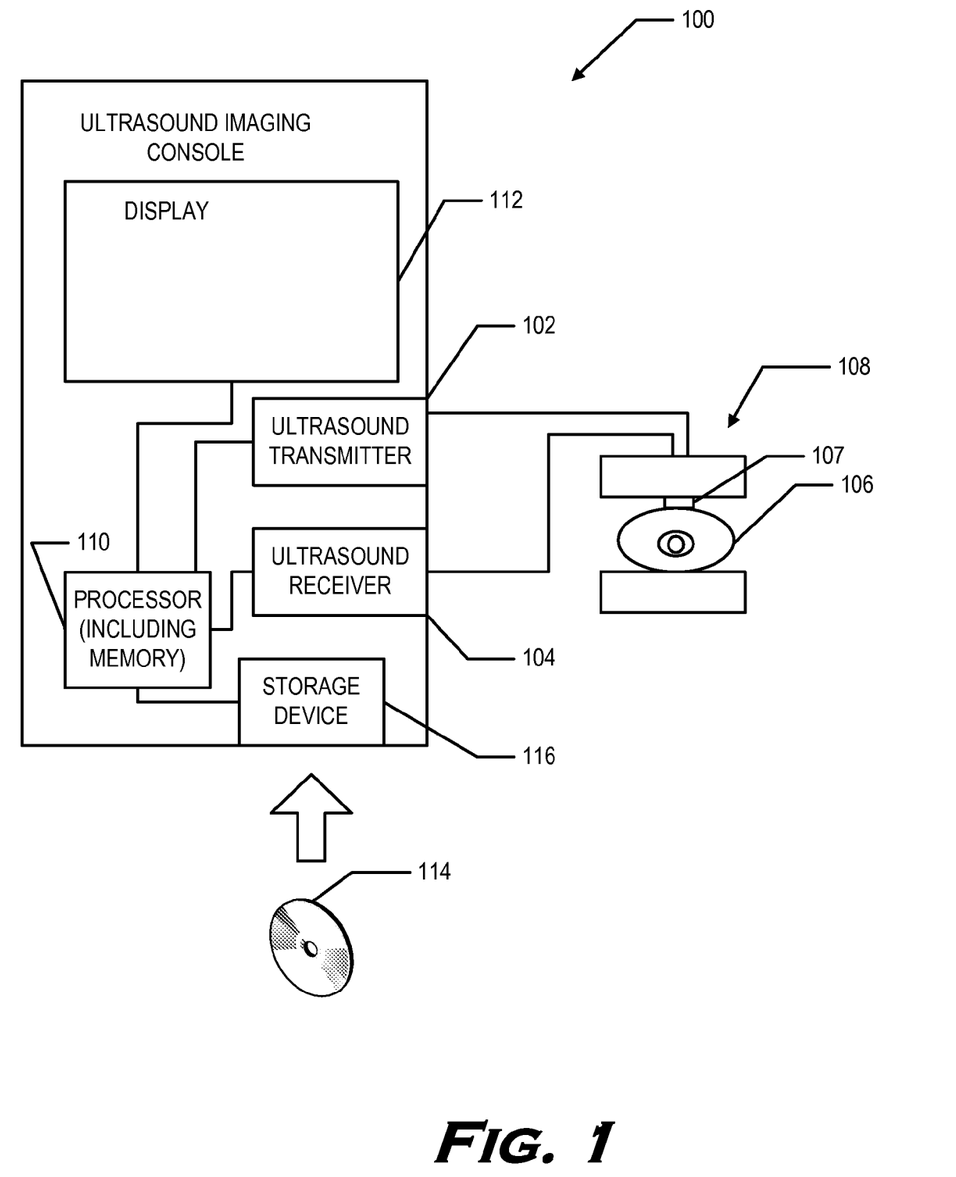
FIG. 1 is a block diagram of an embodiment of an ultrasound imaging apparatus of the present invention.

FIG. 1 is a drawing of an embodiment of an ultrasound imaging device 100. Ultrasound imaging device 100 includes an ultrasound transmitter 102 and an ultrasound receiver 104 configured to receive reflected ultrasound waves reflected from a region of interest of an elastic material 106 and to convert received ultrasound waves into image data. To emit ultrasound waves into the elastic material 106 and to receive reflected ultrasound waves therefrom, an ultrasound probe 107 can be affixed to a compression fixture 108 that is configured to compress material 106 while image data is being collected. Alternate mounting configurations for ultrasound probe 107 include, but are not limited to recessing the probe into a portion of compression fixture 108 and providing an ultrasound probe 107 that is held in place other than on blocks of compression fixture 108. However, a compression fixture 108 is not required by all embodiments of the present invention, as methods and apparatus of the present invention may be applied in freehand examinations.

Ultrasound imaging device 100 also includes a processor 110 configured to analyze the image data, and a display 112 configured to show results from the analysis of the image data. Processor 110 can be a module comprising a computational/logic engine (e.g., a microprocessor or CPU) together with memory, not shown separately in FIG. 1.

In some embodiments of the present invention, a storage device 116 is configured to read instructions from an external medium or media 114 such as CD-ROM, DVD, floppy disks, or other types of machine readable media known in the art. Instructions on medium or media 114 are configured to instruct ultrasound imaging device 100, for example, via processor 110, to perform a method such as illustrated in flow chart 200 of FIG. 2. Flow chart 200 is illustrative of a method embodiment of the present invention in which mechanical properties of an elastic material 106 are assessed.

Figure 2A:
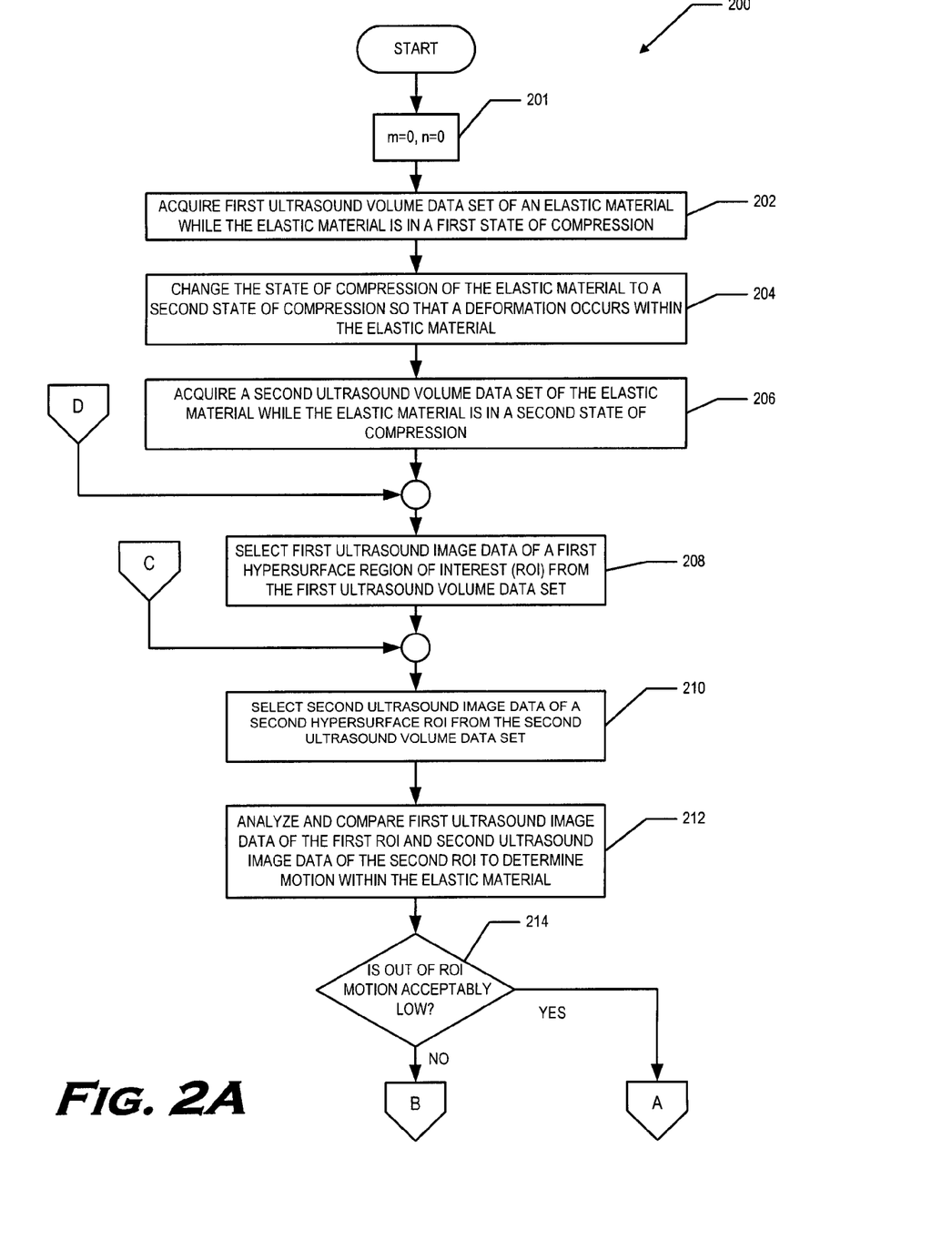
FIG. 2 is a flow chart of a method embodiment of the present invention.
Figure 2B:
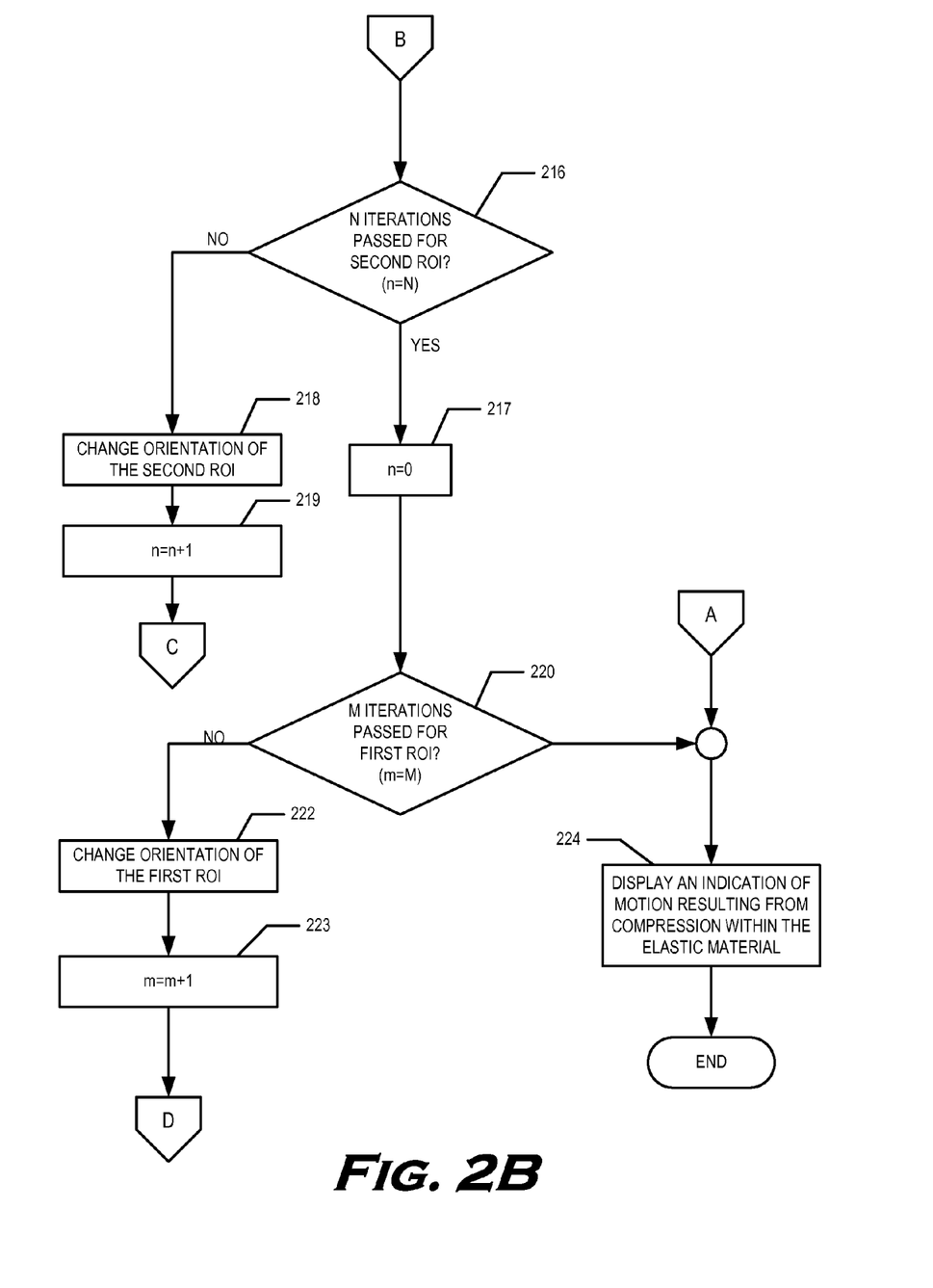

The method embodiment represented by FIG. 2 includes, at 201, setting iteration variables m and n to zero. Next, the method includes, at 202, acquiring first volumetric ultrasound data set of the elastic material 106 while the elastic material is in a first state of compression. For example, in the first state of compression, the elastic material may be uncompressed.

Then, at 204, the state of compression of the elastic material is changed to a second state of compression so that a deformation occurs within the elastic material 106 relative to the first state of compression. Embodiments of the present invention require only that the first state of compression and the second state of compression be different. In some embodiments, as a matter of design choice and/or for other reasons, one of the states of compression may be an uncompressed state and the other an uncompressed state.

At 206, second volumetric ultrasound data set of the elastic material is acquired. At 208 and 210, ultrasound image data in the first hypersurface region of interest (e.g., a plane) and the second hypersurface region of interest are selected from the first ultrasound volume data set and the second ultrasound volume data set, respectively.

At 212, the ultrasound image data in the first ROI and the ultrasound image data in the second ROI are analyzed and compared to determine motion within elastic material 106. If the out of ROI motion resulting from compression is acceptably low at 214, e.g., no greater than a predetermined or selected amount, then, at 224, the analysis and comparison at 212 is used to display an indication of motion resulting from the applied compression within elastic material 106. Otherwise, in some embodiments of the present invention, the process is repeated at 216 for a predefined number of N iterations, where the orientation of the second ROI is changed at 218, the value of iteration counter n is incremented at 219, and the second ultrasound image data ROI is replaced for subsequent analysis at 210 by ultrasound image data in the new, reoriented second ROI. If the predefined number of N iterations is reached, in some embodiments, the iteration counter n is set to 0 at 217 and the process is repeated for a predefined number of M iterations at 220, where the orientation of the first ROI is changed at 222, iteration counter m is incremented at 223, and the first ultrasound image data ROI is replaced for subsequent analysis at 208 by ultrasound image data in the new, reoriented first ROI. When the M iterations of the outer loop that includes 220 is reached, out of ROI motion is presumed to be too high and the process continues at 224 by displaying that the motion is too large to accurately indicate.

This method of assessing mechanical properties of an elastic material 106 can be used for various types of elastic material, such as animal tissue in a veterinary environment, meat in a food service or supply environment, and human tissue in a medical or surgical environment. Embodiments of the present invention in which elastic material 106 is a human breast are of particular interest, in that such embodiments can be useful for detecting cancerous tissue.

In some embodiments of the present invention, the second ROI location is changed adaptively in accordance with selected or preselected optimization criteria, which may include the amount and/or spatial or linear extent of out of ROI tissue motion. In other embodiments, the changed second ROI location is selected from among a set of preselected locations. For example, the ROI used for the second ultrasound image data is limited to that of the first ultrasound image data plus a tilt of 0, 10, 20, 30, 40, 50, 60, 70, 80, or 90 degrees.

Any known method of 2D elastic motion determination may be used to display an indication of such motion. For example, correlations between the first ultrasound image data and the second ultrasound image data may be used to display tissue motion. Tissue motion can also be determined by speckle tracking. In some embodiments of the present invention, the indication of motion within the tissue is displayed as a 2D strain image, wherein an indication of the derivative of the motion is displayed.

In some embodiments of the present invention an ROI with arbitrary orientation is selected from a volume data set. This procedure yields enhanced estimation results compared to conventional 2D strain imaging because out of ROI motion is minimized by adapting the ROI to the direction of tissue motion.

Figure 3:
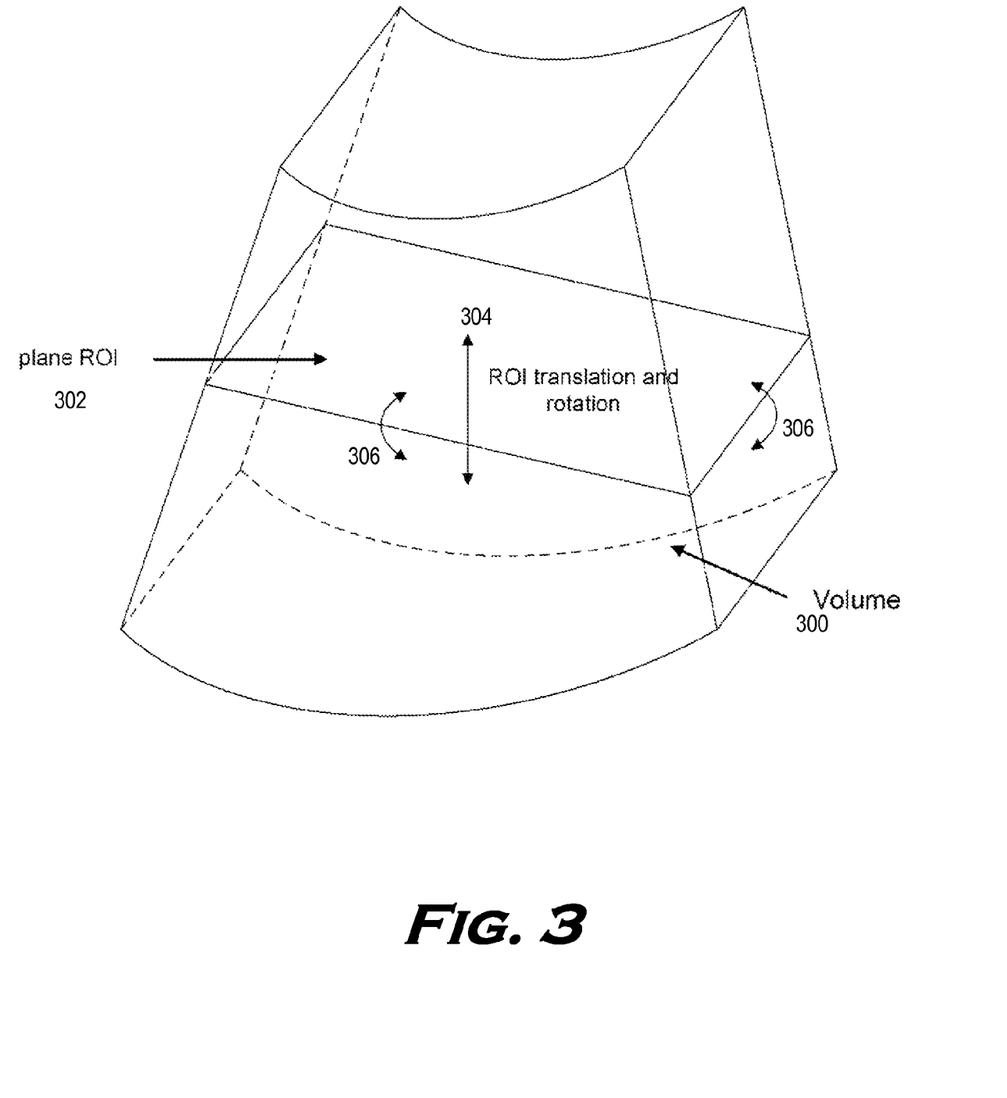
FIG. 3 is a drawing illustrating the geometry of a volume of image data acquired by a volumetric ultrasound imaging device

FIG. 3 is a drawing illustrating the geometry of a volume of image data 300 acquired by a volumetric ultrasound imaging device 100. The hypersurface region of interest (ROI) 302 is located within the volume data set. After compression is applied, elastic material 106 moves differentially depending upon its local composition and/or structure and a second volume data set is acquired. To best capture this movement, ROI 302 is translated 304 and/or rotated 306 in the second volume data set so that motion outside of the translated and/or rotated ROI 302 is either minimized or at least within a specified or predetermined amount. Because the second ultrasound image data is also volumetric, there is no need to perform another ultrasound image data acquisition. Instead, the reorientation of ROI 302 can be performed by selecting appropriate portions of the second ultrasound image data. Usually, the best orientation can be determined within five or six iterations or less, so the movement display can be updated so rapidly that any delay is essentially imperceptible to an observer. For simplicity, the ROI in FIG. 3 is shaped as a plane. However, the ROI can be a hypersurface, and thus may have an arbitrary shape and curvature.

Figure 4:
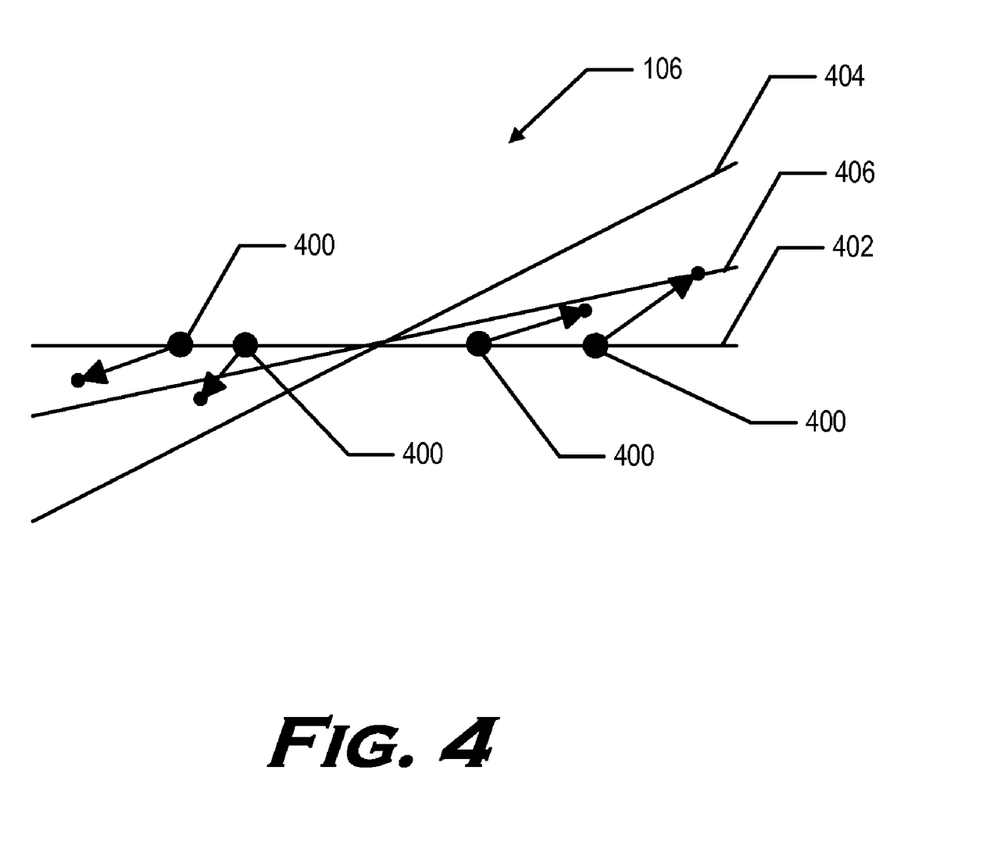
FIG. 4 is a drawing illustrating an instance of movement of identifiable portions of an elastic material of a first region of interest (ROI) when compression is applied.

FIG. 4 is a drawing illustrating the movement of identifiable portions 400 of elastic material 106 off a first ROI 402 when compression is applied. An initial guess at a second ROI is ROI 404. However, once this initial guess is analyzed, it will be found that the out of ROI motion of the identifiable portions 400 exceeds a specified or predetermined amount.

Thus, the process represented by flow chart 200 will eventually converge on a better choice for the second ROI, namely, ROI 406.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method for assessing mechanical properties of an elastic material using an ultrasound imaging device having an ultrasound transmitter, an ultrasound receiver configured to receive reflected ultrasound waves reflected from a region of interest of the elastic material and to convert the received ultrasound waves into image data, a processor configured to analyze the image data, and a display configured to show results from said analysis of the image data, said method comprising:
obtaining a first volumetric ultrasound data set of the elastic material while the elastic material is in a first state of compression and obtaining a second volumetric ultrasound data set of the elastic material while the elastic material is in the second state of compression;
selecting first ultrasound image data of a first hypersurface region of interest (ROI) from the first ultrasound volume data set and selecting second ultrasound image data of a second hypersurface ROI from the second ultrasound volume data set;
comparing the first ultrasound image data and the second ultrasound image data to determine motion within the elastic material; and
determining whether out of ROI motion of the elastic material is less than a predetermined amount, and,
if not, and if an allowed number of iterations has not been met, then changing an orientation of at least one of said ROIs and iterating a corresponding said selection of ultrasound image data, as well as iterating said analyzing and comparing the first ultrasound image data and the second ultrasound image data and said test of out of ROI motion,
or otherwise, displaying an indication of motion resulting from compression within the elastic material.

2. The method of claim 1 wherein the material is animal tissue.

3. The method of claim 1 wherein the material is meat.

4. The method of claim 1 wherein the material is human tissue.

5. The method of claim 4 wherein the material is a human breast.

6. The method of claim 1 further comprising changing a location of at least the first ROI or the second ROI adaptively in accordance with selected or preselected optimization criteria.

7. The method of claim 1 further comprising selecting changed ROI locations from among a set of preselected locations.

8. The method of claim 1 where the hypersurface region of interest is a plane.

9. An ultrasound imaging apparatus comprising:
an ultrasound transmitter;

an ultrasound receiver configured to receive reflected ultrasound waves reflected from a region of interest in an elastic material and to convert the received ultrasound waves into image data;

a processor configured to analyze the image data;

and a display configured to show results from said analysis of the image data, said image apparatus configured to:

obtain a first volumetric ultrasound data set of the elastic material while the elastic material is in a first state of compression and obtain a second volumetric ultrasound data set of the elastic material while the elastic material is in a second state of compression;

select first ultrasound image data of a first hypersurface region of interest (ROI) from the first ultrasound volume data set and select second ultrasound image data of a second hypersurface ROI from the second ultrasound volume data set;

compare the first ultrasound image data and the second ultrasound image data to determine motion within the elastic material; and determine whether out of ROI motion of the elastic material is less than a predetermined amount, and, if not, and if an allowed number of iterations has not been met, then change an orientation of at least one of said ROIs and iterate a corresponding said selection of ultrasound image data, as well as iterate said analyzing and comparing the first ultrasound image data and the second ultrasound image data and said test of out of ROI motion, or otherwise, display an indication of motion resulting from compression within the elastic material.

10. The apparatus of claim 9 further configured to change the location of at least the first ROI or the second ROI adaptively in accordance with selected or preselected optimization criteria.

11. The apparatus of claim 9 further configured to select the changed ROI locations from among a set of preselected locations.

12. The apparatus of claim 9 further configured to determine tissue motion by correlation of image data.

13. The apparatus of claim 9 further configured to determine tissue motion by speckle tracking.

14. The apparatus of claim 9 further configured to display a strain image.

15. A non-transitory machine-readable medium or media having thereon instructions configured to instruct an ultrasound imaging device having an ultrasound transmitter, an ultrasound receiver configured to receive reflected ultrasound waves reflected from a region of interest in an elastic material and to convert the received ultrasound waves into image data, a processor configured to analyze the image data, and a display configured to show results from said analysis of the image data to:

obtain a first volumetric ultrasound data set of the elastic material while the elastic material is in a first state of compression;

obtain a second volumetric ultrasound data set of the elastic material while the elastic material is in a second state of compression;

select first ultrasound image data of a first hypersurface region of interest (ROI) from the first ultrasound volume data set;

select second ultrasound image data of a second hypersurface ROI from the second ultrasound volume data set;

analyze and compare the first ultrasound image data and the second ultrasound image data to determine motion within the elastic material; and test whether out of ROI motion of the elastic material is less than a specified or predetermined amount, and, if not, and if an allowed number of iterations has not been met, then change an orientation of at least one of said ROIs and iterate a corresponding said selection of ultrasound image data, as well as iterate said analyzing and comparing the first ultrasound image data and the second ultrasound image data and said test of out of ROI motion, or otherwise, display an indication of motion resulting from compression within the elastic material.

16. The non-transitory machine readable medium or media of claim 15 wherein said instructions are further configured to instruct the ultrasound imaging apparatus to change a location of at least the first ROI or the second ROI adaptively in accordance with selected or preselected optimization criteria.

17. The non-transitory machine readable medium or media of claim 15 wherein said instructions are further configured to instruct the ultrasound imaging apparatus to select the changed ROI locations from among a set of preselected locations.

18. The non-transitory machine readable medium or media of claim 15 wherein said instructions are further configured to instruct the ultrasound imaging apparatus to determine tissue motion by correlation of image data.

19. The non-transitory machine readable medium or media of claim 15 wherein said instructions are further configured to instruct the ultrasound imaging apparatus to determine tissue motion by speckle tracking.

20. The non-transitory machine readable medium or media of claim 15 wherein said instructions are further configured to instruct the ultrasound imaging apparatus to display a strain image.

* * * * *